United States Patent
Oh et al.

(10) Patent No.: US 9,381,680 B2
(45) Date of Patent: Jul. 5, 2016

(54) METHOD OF MANUFACTURING SOLID SOLUTION PERFORATOR PATCHES AND USES THEREOF

(75) Inventors: Sea-Jin Oh, Palo Alto, CA (US); Sung-Yun Kwon, Fremont, CA (US)

(73) Assignee: TheraJect, Inc., Fremont, CA (US)

( * ) Notice: Subject to any disclaimer, the term of this patent is extended or adjusted under 35 U.S.C. 154(b) by 1173 days.

(21) Appl. No.: 12/994,148

(22) PCT Filed: May 21, 2009

(86) PCT No.: PCT/US2009/003145
§ 371 (c)(1),
(2), (4) Date: Feb. 4, 2011

(87) PCT Pub. No.: WO2009/142741
PCT Pub. Date: Nov. 26, 2009

(65) Prior Publication Data
US 2011/0121486 A1    May 26, 2011

Related U.S. Application Data

(60) Provisional application No. 61/128,405, filed on May 21, 2008.

(51) Int. Cl.
| B29C 33/38 | (2006.01) |
| A61M 37/00 | (2006.01) |
| B29C 33/30 | (2006.01) |
| B29C 33/00 | (2006.01) |
| A61B 17/20 | (2006.01) |
| A61B 17/00 | (2006.01) |

(52) U.S. Cl.
CPC ........... *B29C 33/3885* (2013.01); *A61B 17/205* (2013.01); *A61M 37/0015* (2013.01); *B29C 33/0027* (2013.01); *B29C 33/0033* (2013.01); *B29C 33/308* (2013.01); *B29C 33/3878* (2013.01); *A61B 2017/00345* (2013.01); *A61B 2017/00761* (2013.01); *A61M 2037/0023* (2013.01); *A61M 2037/0046* (2013.01); *A61M 2037/0053* (2013.01); *A61M 2037/0061* (2013.01)

(58) Field of Classification Search
CPC ................................ A61M 2037/0053
USPC .................... 264/220, 225, 226, 227
See application file for complete search history.

(56) References Cited

U.S. PATENT DOCUMENTS

| 3,072,122 A | 1/1963 | Rosenthal |
| 3,167,073 A | 1/1965 | Rosenthal |

(Continued)

FOREIGN PATENT DOCUMENTS

| EP | 1301238 B1 | 9/2004 |
| EP | 1512429 B1 | 9/2005 |

(Continued)

*Primary Examiner* — Atul P. Khare
(74) *Attorney, Agent, or Firm* — Brinks Gilson & Lione

(57) ABSTRACT

Methods for fabricating and manufacturing solid solution perforators (SSPs) using sharp metal or glass needles and/or subsequent molding and use are described. The methods entail making microneedles by various precision machining techniques and micromold structures from curable materials. Various designs of patch, cartridge and applicator are described. Also described are methods for adjusting the microneedle mechanical strength using formulation and/or post-drying processes.

14 Claims, 12 Drawing Sheets

(56) References Cited

U.S. PATENT DOCUMENTS

| | | |
|---|---|---|
| 3,596,660 A | 8/1971 | Melone |
| 3,814,097 A | 6/1974 | Ganderton et al. |
| 3,905,371 A | 9/1975 | Stickl et al. |
| 3,964,482 A | 6/1976 | Gerstel et al. |
| 4,109,655 A | 8/1978 | Chacornac |
| 4,592,753 A | 6/1986 | Panoz |
| 4,732,453 A | 3/1988 | de Montebello et al. |
| 4,798,582 A | 1/1989 | Sarath et al. |
| 4,936,835 A | 6/1990 | Haaga |
| 4,966,159 A | 10/1990 | Maganias |
| 5,250,023 A | 10/1993 | Lee et al. |
| 5,262,128 A | 11/1993 | Leighton et al. |
| 5,279,544 A | 1/1994 | Gross et al. |
| 5,383,512 A | 1/1995 | Jarvis |
| 5,445,611 A | 8/1995 | Eppstein et al. |
| 5,457,041 A | 10/1995 | Ginaven et al. |
| 5,458,140 A | 10/1995 | Eppstein et al. |
| 5,527,288 A | 6/1996 | Gross et al. |
| 5,591,139 A | 1/1997 | Lin et al. |
| 5,695,484 A | 12/1997 | Cox |
| 5,749,376 A | 5/1998 | Wilk et al. |
| 5,843,114 A | 12/1998 | Jang |
| 5,848,991 A | 12/1998 | Gross et al. |
| 5,855,211 A | 1/1999 | Nelson |
| 5,855,801 A | 1/1999 | Lin et al. |
| 5,879,326 A | 3/1999 | Godshall et al. |
| 5,928,207 A | 7/1999 | Pisano et al. |
| 5,983,136 A | 11/1999 | Kamen |
| 5,990,194 A | 11/1999 | Dunn et al. |
| 6,013,050 A | 1/2000 | Bellhouse et al. |
| 6,030,404 A | 2/2000 | Lawson et al. |
| 6,050,988 A | 4/2000 | Zuck |
| 6,083,196 A | 7/2000 | Trautman et al. |
| 6,091,975 A | 7/2000 | Daddona et al. |
| 6,102,896 A | 8/2000 | Roser |
| 6,106,751 A | 8/2000 | Talbot et al. |
| 6,132,755 A | 10/2000 | Eicher et al. |
| 6,142,939 A | 11/2000 | Eppstein et al. |
| 6,187,210 B1 | 2/2001 | Lebouitz et al. |
| 6,219,574 B1 | 4/2001 | Cormier et al. |
| 6,230,051 B1 | 5/2001 | Cormier et al. |
| 6,256,533 B1 | 7/2001 | Yuzhakov et al. |
| 6,312,612 B1 | 11/2001 | Sherman et al. |
| 6,322,808 B1 | 11/2001 | Trautman et al. |
| 6,331,266 B1 | 12/2001 | Powell et al. |
| 6,331,310 B1 | 12/2001 | Roser et al. |
| 6,334,856 B1 | 1/2002 | Allen et al. |
| 6,335,149 B1 | 1/2002 | Xu et al. |
| 6,352,506 B1 | 3/2002 | Eppstein et al. |
| 6,352,722 B1 | 3/2002 | Blair |
| 6,375,776 B1 | 4/2002 | Buoni et al. |
| 6,379,324 B1 | 4/2002 | Gartstein et al. |
| 6,406,455 B1 | 6/2002 | Willis et al. |
| 6,440,096 B1 | 8/2002 | Lastovich et al. |
| 6,485,453 B1 | 11/2002 | Buch-Rasmussen et al. |
| 6,532,386 B2 | 3/2003 | Sun et al. |
| 6,607,513 B1 | 8/2003 | Down et al. |
| 6,611,707 B1 | 8/2003 | Prausnitz et al. |
| 6,656,147 B1 | 12/2003 | Gertsek et al. |
| 6,663,820 B2 * | 12/2003 | Arias et al. ............ 264/496 |
| 6,743,211 B1 | 6/2004 | Prausnitz et al. |
| 6,855,478 B2 | 2/2005 | DeVoe et al. |
| 6,881,203 B2 | 4/2005 | Delmore et al. |
| 6,899,838 B2 * | 5/2005 | Lastovich ............ 264/102 |
| 6,924,087 B2 | 8/2005 | Yeshurun et al. |
| 6,945,952 B2 | 9/2005 | Kwon |
| 7,211,062 B2 | 5/2007 | Kwon |
| 7,699,819 B2 | 4/2010 | Yeung et al. |
| 7,918,814 B2 | 4/2011 | Prausnitz et al. |
| 8,062,573 B2 * | 11/2011 | Kwon ............ 264/319 |
| 8,088,321 B2 * | 1/2012 | Ferguson et al. ......... 264/328.7 |
| 8,197,435 B2 | 6/2012 | Prausnitz et al. |
| 8,398,397 B2 | 3/2013 | Fischer |
| 8,561,795 B2 | 10/2013 | Schott |
| 8,603,384 B2 * | 12/2013 | Luttge et al. ............ 264/337 |
| 8,606,366 B2 | 12/2013 | Flyash et al. |
| 8,636,713 B2 | 1/2014 | Prausnitz et al. |
| 8,734,697 B2 | 5/2014 | Chen et al. |
| 8,808,202 B2 | 8/2014 | Brancazio |
| 8,808,225 B2 | 8/2014 | Prausnitz et al. |
| 8,821,412 B2 | 9/2014 | Gonzalez-Zugasti et al. |
| 8,821,446 B2 | 9/2014 | Trautman et al. |
| 8,827,971 B2 | 9/2014 | Gonzalez-Zugasti et al. |
| 8,858,807 B2 * | 10/2014 | Devoe et al. ............ 216/11 |
| 8,883,015 B2 | 11/2014 | Kendall et al. |
| 8,900,231 B2 | 12/2014 | Kreindel |
| 8,906,015 B2 | 12/2014 | Kreindel |
| 8,911,749 B2 | 12/2014 | Ghartey-Tagoe et al. |
| 8,920,696 B2 | 12/2014 | Lee |
| 9,033,898 B2 | 5/2015 | Chickering, III et al. |
| 9,041,541 B2 | 5/2015 | Levinson et al. |
| 9,084,587 B2 | 7/2015 | Eckhouse et al. |
| 9,113,836 B2 | 8/2015 | Bernstein et al. |
| 9,114,238 B2 | 8/2015 | Singh et al. |
| 9,119,578 B2 | 9/2015 | Haghgooie et al. |
| 2001/0038858 A1 | 11/2001 | Roser et al. |
| 2001/0053891 A1 | 12/2001 | Ackley |
| 2002/0006355 A1 | 1/2002 | Whitson |
| 2002/0009464 A1 | 1/2002 | Colaco |
| 2002/0012687 A1 | 1/2002 | Roser et al. |
| 2002/0016562 A1 | 2/2002 | Cormier et al. |
| 2002/0020688 A1 | 2/2002 | Sherman et al. |
| 2002/0058067 A1 | 5/2002 | Blair |
| 2002/0066978 A1 | 6/2002 | Kim et al. |
| 2002/0082543 A1 | 6/2002 | Park et al. |
| 2002/0110585 A1 | 8/2002 | Godbey et al. |
| 2002/0146540 A1 | 10/2002 | Johnston et al. |
| 2002/0177839 A1 | 11/2002 | Cormier et al. |
| 2003/0025227 A1 | 2/2003 | Daniell |
| 2003/0083645 A1 | 5/2003 | Angel et al. |
| 2003/0148291 A1 | 8/2003 | Robotti |
| 2004/0049150 A1 | 3/2004 | Dalton et al. |
| 2004/0186419 A1 | 9/2004 | Cho |
| 2004/0199103 A1 | 10/2004 | Kwon |
| 2005/0065463 A1 | 3/2005 | Tobinaga et al. |
| 2005/0137531 A1 | 6/2005 | Prausnitz et al. |
| 2005/0137536 A1 | 6/2005 | Gonnelli |
| 2005/0251088 A1 * | 11/2005 | Kwon ............ 604/60 |
| 2006/0074376 A1 | 4/2006 | Kwon |
| 2006/0202385 A1 | 9/2006 | Xu et al. |
| 2007/0293815 A1 | 12/2007 | Chan et al. |
| 2008/0027384 A1 | 1/2008 | Wang et al. |
| 2008/0063866 A1 * | 3/2008 | Allen et al. ............ 428/389 |
| 2008/0138583 A1 * | 6/2008 | Bhandari et al. ............ 428/156 |
| 2008/0269666 A1 | 10/2008 | Wang et al. |
| 2009/0035446 A1 | 2/2009 | Kwon |
| 2010/0210993 A1 | 8/2010 | Flyash et al. |
| 2010/0256597 A1 | 10/2010 | Prausnitz et al. |
| 2012/0015069 A1 | 1/2012 | Lee |
| 2012/0193840 A1 | 8/2012 | Kwon |
| 2014/0316333 A1 | 10/2014 | Kwon |
| 2014/0371713 A1 | 12/2014 | Quan et al. |
| 2015/0112250 A1 | 4/2015 | Kwon |

FOREIGN PATENT DOCUMENTS

| | | |
|---|---|---|
| JP | 2003-238347 | 8/2003 |
| JP | 2003238347 | 8/2003 |
| JP | 2005-501615 | 1/2005 |
| JP | 2009-535122 | 10/2009 |
| WO | WO 99/27852 A1 | 6/1999 |
| WO | WO 2004/000389 A2 | 12/2003 |
| WO | WO 2005/000382 A2 | 1/2005 |
| WO | WO 2005/105401 A1 | 11/2005 |
| WO | WO 2005105401 A1 * | 11/2005 |
| WO | WO 2006/128034 A1 | 11/2006 |
| WO | WO 2007/030477 A2 | 3/2007 |
| WO | WO 2007030477 A2 * | 3/2007 |
| WO | WO 2007/112309 A2 | 10/2007 |
| WO | WO 2007/131050 A1 | 11/2007 |
| WO | WO 2008/011625 A2 | 1/2008 |
| WO | WO 2008011625 A2 * | 1/2008 ............ A61K 9/0021 |
| WO | WO 2008/072229 A2 | 6/2008 |
| WO | WO 2008/130587 A2 | 10/2008 |

(56) References Cited

FOREIGN PATENT DOCUMENTS

| WO | WO 2009/049243 A2 | 4/2009 |
| WO | WO 2009/142741 A1 | 11/2009 |
| WO | WO 2010/071918 A1 | 7/2010 |
| WO | WO 2010/078323 A1 | 7/2010 |
| WO | WO 2010078323 A1 * | 7/2010 |
| WO | WO 2011/014607 A1 | 2/2011 |
| WO | WO 2011/076537 A1 | 6/2011 |
| WO | WO 2011/163347 A2 | 12/2011 |
| WO | WO 2011/135530 A2 | 11/2012 |
| WO | WO 2012/153266 A2 | 11/2012 |
| WO | WO 2013/063614 A1 | 5/2013 |
| WO | WO 2013/131643 A2 | 9/2013 |
| WO | WO 2013/152092 A1 | 10/2013 |
| WO | WO 2014/144973 A1 | 9/2014 |
| WO | WO 2015/084735 A2 | 6/2015 |

* cited by examiner

Before treatment

After two days

METHOD OF MANUFACTURING SOLID SOLUTION PERFORATOR PATCHES AND USES THEREOF

CROSS-REFERENCE TO RELATED APPLICATIONS

This application is a National Stage Patent Application of International Patent Application No. PCT/US2009/003145 (filed on May 21, 2009) under 35 U.S.C. §371, which claims priority to U.S. Provisional Application No. 61/128,405 (filed on May 21, 2008), which are all hereby incorporated by reference in their entirety.

TECHNICAL FIELD

The present invention relates generally to a method for fabricating and manufacturing solid solution perforators (SSPs) such as dissolving microneedles using sharp metal or glass needles or precision machining and/or subsequent molding. More particularly, the invention relates to a method of creating micromold structures made of curable materials, from fine needle array alignments, and uses thereof. Additionally, the invention relates to methods for increasing mechanical strength of microneedles, designing flexible microneedle patches, and patch injection/insertion and uses thereof.

BACKGROUND OF THE INVENTION

Transdermal or intradermal delivery of drugs, including protein and vaccine delivery, is a very effective method for achieving systemic or localized pharmacological effects. However, there are barriers involved in providing sufficient drug penetration across the skin. Skin consists of multiple layers. The stratum corneum is the outermost layer, then there is a viable epidermal layer, and finally a dermal tissue layer. The thin layer of stratum corneum of 10-50 µm represents a major barrier for drug delivery through the skin. The stratum corneum is responsible for 50%-90% of the skin barrier property against transdermal drug delivery, depending upon the physical and chemical properties of the drug material, in particular, lipophilicity and molecular weight.

The use of microneedles in transdermal and intradermal delivery is advantageous as intracutaneous drug delivery or drug sampling can be accomplished by reducing the above barrier without pain and bleeding. As used herein, the term "microneedles" refers to a plurality of elongated structures that are sufficiently long to penetrate through the stratum corneum skin layer into the epidermal or dermal or subcutaneous layer. In general, the microneedles are not so long as to penetrate into the dermal layer, although there are circumstances where penetrating the dermal layer would be necessary or desirable. The use of microneedles as an alternative to the use of hypodermic needles for drug delivery by injection is disclosed in U.S. Pat. No. 3,964,482, in which an array of either solid or hollow microneedles is used to penetrate through the stratum corneum and into the epidermal layer. Fluid is dispensed either through the hollow microneedles or through permeable solid projections, or perhaps around non-permeable solid projections that are surrounded by a permeable material or an aperture. A membrane material is used to control the rate of drug release, and the drug transfer mechanism is absorption.

Other types of microneedle and microblade structures are disclosed in PCT Publications Nos. WO 98/00193, WO 97/48440, WO 97/48441, WO 97/48442 and WO 96/37256.

Microneedles (less than 1 mm in diameter) have been used to effect percutaneous drug delivery. Microneedles have also been used to deliver a drug through a lumen in the needles, to deliver a drug along the outside of the needle shafts, or as skin perforators for subsequent patch drug application. Silicon microneedles, for example, have been developed using the microfabrication method or MicroElectroMechanicalSystems (MEMS) fabrication method. Examples are described in U.S. Pat. Nos. 6,334,856, 6,256,533, 6,312,612 and 6,379,324. Unfortunately, silicon needles are not dissolvable in the skin, can break during use and stay in the skin tissue, producing considerable irritation and even infection. Non-silicon microneedles have also been developed. Examples are described in U.S. Pat. Nos. 6,334,856 and 6,091,975. However, microneedles that are made of metal or plastic are insoluble or slowly dissolve (i.e., in less than several hours) in the skin, and are therefore generally used for providing a microconduit to transport drug from a drug reservoir, or for creating micropores.

Typically, microneedles are fabricated by the MEMS fabrication method. The use of polydimethylsilozane (PDMS) mold for casting polymeric microneedles is disclosed in U.S. Pat. Nos. 6,663,820 and 6,334,856 in which the positive matter of microneedles is fabricated by using MEMS technology. However, MEMS fabrication for the master microneedle array can be expensive and complicated. Moreover, the polymeric microneedles may require drug loading or drug coating, rendering the casting methods unsuitable for mass production.

SUMMARY OF THE INVENTION

The present invention overcomes these problems and provides inexpensive and uncomplicated methods for manufacturing SSP drug delivery systems including dissolvable microneedles. In particular, the invention provides a method for constructing positive microneedle master molds made from an array of various types of fine needles.

The microneedles for use in the present invention are made by making a mold from a metal, polymer, or glass (or other extendable) material wire. For making a positive master mold from an alignment needle, the individual needles for the positive master are made by, for example, grinding a wire end or pulling a wire and then sharpening. Other suitable methods for making sharp needles are known and will find use herein. The needles may have various shapes, for example, round in cross-section or square in cross-section. The individual needles from wires are integrated or arranged into the master structure relatively quickly and with much less expense than making a negative mold which is used to cast the final dissolving microneedles.

Following is an exemplary procedure for arranging microneedles in a substrate having a hole array. The integration of needles in the hole plates include: (1) parallel alignment of first and second plates having hole arrays and (2) passing needles through holes of the first and second plates to desired, preselected protrusion lengths above the second plate. The needle tip positioning can be done by (1) using a stop wall at the desired distance from the second plate, (2) using tapered holes in the second plate, or (3) using an individually addressable actuator array that moves individual needles.

Another method for constructing a positive master mold is by precision machining, such as Computer Numerical Control (CNC) milling, grinding or drilling. See, e.g., CNC Machining Handbook, James Madison, Industrial Press, Inc., 1991; and An Introduction to CNC Machining and Programming, Gibbs and Crandell, Industrial Press, Inc. 1996, for a discussion of CNC methods. For example, from a block of steel, two trench arrays can be cut in two perpendicular directions with predetermined side-wall angles and an array of pyramid shaped microneedles can be generated with desired side angles.

Another method for constructing a positive master mold is to cast microneedles from a negative mold fabricated by the MEMS fabrication method or the CNC precision machining method such as by drilling or grinding. From the master microneedle array structure, a mold, called a "negative mold" herein, can be made and used for fabricating dissolvable SSPs. The dissolvable system includes a solid matrix of dissolvable (including meltable) material that optionally holds one or more selected drugs and is formed into one or more perforators from the negative mold. The matrix can be composed of fast-dissolving and/or swelling materials. The solid solution can be a homogeneous, non-homogeneous, suspension solution with a different drug loading phase. In order to make the dissolving SSPs, a positive master prototype is first manufactured with the methods described above. A negative mold of silicone or curable materials is then fabricated from the positive master. In particular, the secondary silicone negative mold fabrication allows cost-effective mass production and utilizes the inherent properties of silicone materials, such as surface tension, flexibility, gas-permeation, and the like. In another embodiment, the silicone negative mold is not separated from the microneedle array until the microneedle array is used. In this embodiment, the silicone mold is used as packaging material to keep the microneedle array intact because the silicone material is reasonably inexpensive.

In another embodiment of the negative mold, the microneedle cavity in the negative mold has an open end at the cavity bottom corner to easily fill the cavity with gel by applying a vacuum through the hole or even by pressing gel into the cavity.

The SSP microneedle array including drug is fabricated by casting a drug-containing hydrogel or like moldable material in the negative silicone mold. In preparing the solid solution, the drug can be concentrated into the microneedle tip by a casting and centrifuging process, such as described in PCT Publication No. WO 07/030,477, incorporated herein by reference in its entirety. By "microneedle tip" is meant the tapered end of the microneedle. Generally, drug will be concentrated in the bottom half to a third of the microneedle, preferably in the bottom quarter or less of the portion of the microneedle that forms the pointed tip. An adhesive layer can be cast between microneedles by a multiple casting/wiping process of the drug gel and adhesive layer. With adhesives (especially water-based adhesives) as a basal layer, the microneedle array becomes sticky except for the microneedle portion and the SSP patch does not need additional sticky peripheral adhesives on the backing film. A flexible layer can be laminated over the sticky layer. The final microneedle will be a flexible and a self-sticky microneedle array. In applying the microneedle patch, the drug-loaded patch is mounted in a cartridge. The cartridge is attached to an injector. The adhesive layer between microneedles can hold the microneedle patch on the skin upon administration of the SSP patch with the injector.

A cartridge can be used in the injection device as described in U.S. Pat. Nos. 6,945,952, 7,182,747 and 7,211,062, incorporated herein by reference in their entireties. The drug-microneedle array patch is attached in the center of the cartridge to bring the microneedle tips into contact with the skin of the injection target. The cartridge is mounted to the end of the injector, such as by rotation-locking, push-fitting, detachable glue, by magnetic attachment, or by using a temporary locking mechanism of the cartridge at the end of the injector. The penetrating depth of the microneedles can be made consistent by hitting the microneedles in the cartridge by the applicator. Typically, the cartridge is flat and thin, preferably not thicker than about 10 mm. The exterior of the cartridge can be in any of various shapes and sizes. The cartridge can be made of moldable plastic. The cartridge may be designed for one-time use and can be disposable. The cartridge can be attached on the injector piston to be moved with the piston to the skin. In one embodiment, the microneedle array is placed close to the target skin instead of onto the piston of the injector. This design is simple for use and mass-production without losing the efficiency. An alternative method for applying the patch is to insert the patch with the thumb or a finger and the insertion force and duration can be controlled by using a pressure sensor film or inserting device.

Another method for penetrating effectively into the skin is to increase the mechanical strength of the microneedles by a formulating and post-drying process of the microneedle. In particular, by adding a mono- or di-saccharide to the matrix polymer, carboxymethyl cellulose, the mechanical strength can be improved. In addition, use of a post-drying process (or removing additional water content from the microneedle matrix) after separating from the mold improves the mechanical strength of the microneedle.

Accordingly, in one embodiment, the invention is directed to a method of manufacturing a microneedle array comprising (a) preparing a positive master mold by positioning microneedles in a defining plate comprising a top and bottom surface, wherein the microneedles are placed at a predetermined distance from one another, and further wherein the microneedle tips protrude from the bottom of the defining plate; (b) preparing a negative mold by either casting a castable material onto the positive master mold or dipping the positive master mold into a curable gel or thermoplastic material, to produce a negative mold having the same surface contour as the positive master mold; (c) adding a dissolvable polymer to the negative mold to form a microneedle array; and (d) drying the microneedle array.

In certain embodiments, all the microneedles positioned in the defining plate protrude the same distance from the bottom of the defining plate. In other embodiments, at least one of the microneedles positioned in the defining plate protrudes a different distance from the bottom of the defining plate than the other microneedles.

In additional embodiments, individual needle lengths in the defining plate are adjusted using an actuator mechanism that moves individual needles to a desired distance through the defining plate. In other embodiments, the microneedle tip is positioned using a stop wall at a desired distance from the defining plate. In yet further embodiments, the microneedle tip is positioned using tapered holes in the defining plate.

In further embodiments, the method further comprises applying a vacuum, centrifuge or compressive force to the negative mold to fill the mold with the dissolvable polymer and/or a selected drug.

In additional embodiments, the method further comprises separating the dried microneedle array from the negative mold.

In yet another embodiment, the invention is directed to a method of manufacturing a microneedle array comprising (a) preparing a positive master mold by drilling, milling or grinding a metal or formable plate in a predetermined direction at a predetermined angle to define a plurality of microneedles; (b) preparing a negative mold by either casting a castable material onto the positive master mold or dipping the positive master mold into a curable gel or thermoplastic material, to produce a negative mold having the same surface contour as the positive master mold; (c) adding a dissolvable polymer to the negative mold to form a microneedle array; and (d) drying the microneedle array. In certain embodiments, the drilling, milling or grinding is done using precision machining, such as by Computer Numerical Control (CNC) milling, grinding or drilling.

In additional embodiments, the methods above further comprise casting an adhesive layer between the microneedles of the microneedle array. In other embodiments, the methods above further comprise casting a flexible and sticky layer on microneedle array.

In further embodiments, the methods above further comprise creating a micro-hole at the microneedle tip of the negative mold.

In certain embodiments of the above methods, the curable gel or castable material is uncured silicone. In other embodiments, the curable gel or castable material is polydimethylsilozane (PDMS).

In additional embodiments, the dissolvable polymer is a hydrogel, such as a hydrogel comprising sodium carboxymethyl cellulose (SCMC).

In certain embodiments, a selected drug and/or vitamin C is added to the negative mold, such as added to a hydrogel that is applied to the negative mold.

In additional embodiments, the invention is directed to a method of manufacturing a microneedle array system comprising (a) manufacturing a microneedle array according to any one of the methods above; and (b) mounting the manufactured microneedle array in a cartridge for delivery to skin. In certain embodiments, the cartridge is in association with an injector.

These and other embodiments of the subject invention will readily occur to those of skill in the art in view of the disclosure herein.

DETAILED DESCRIPTION OF THE INVENTION

The practice of the present invention will employ, unless otherwise indicated, conventional methods of engineering, chemistry, biochemistry, pharmacology and drug delivery, within the skill of the art. Such techniques are explained fully in the literature.

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "a protein" includes a mixture of two or more polypeptides, and the like.

Fabrication of Mold

Figure 1A:
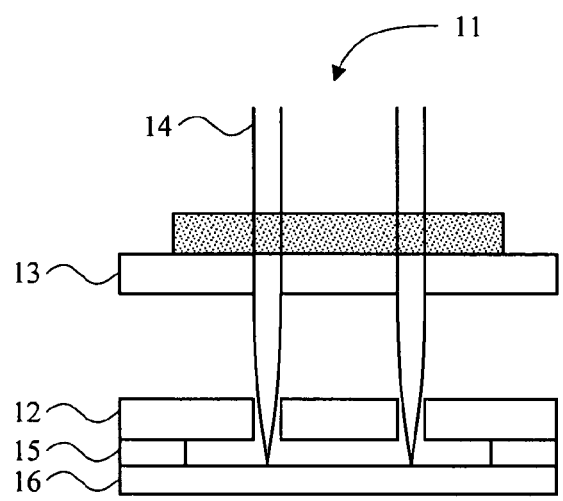
FIGS. 1A, 1B and 1C are magnified representations of a positive master.
Figure 1B:
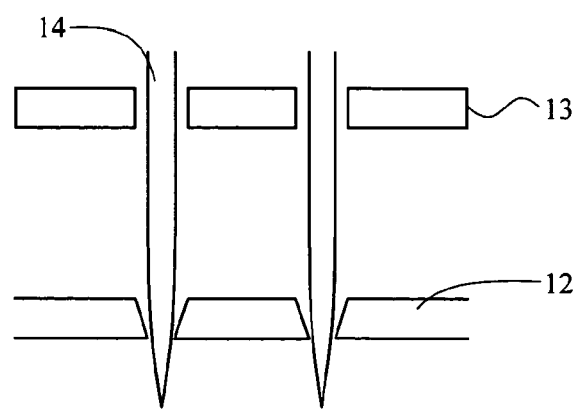
Figure 1C:
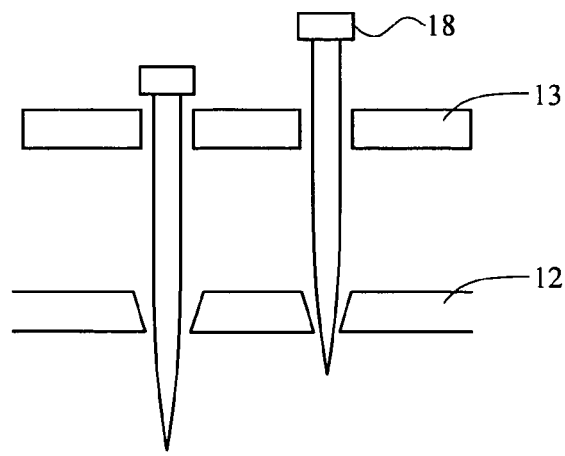

FIGS. 1A-1C show cross-sectional views of positive microneedle array masters for making mold 11, including a hole defining plate 12 with top and bottom surfaces, optional supporting plates 13, a sharp needle 14, spacer 15 for determining the length of microneedles and needle tip alignment plate 16.

A fine metal or glass wire can be sharpened to make sharp needle 14. The fine wire can be any material, including metal, plastic and/or ceramics, including glass. The sharpness is determined by how the needle is prepared. For a metal needle, typically wire is ground to the desired sharpness. For glass or plastic material, a sharp needle is obtained by typically extending wire above the glass transition temperature. In one embodiment, an acupuncture medical needle can be used for making the positive master. The needles can have any of various shapes, such as round cross-section, square cross-section, etc.

The holes in plates 12 and 13 can be drilled, etched or punched. The holes can have any of various shapes that can be made by, for example, photolithography and subsequent etching as used in MEMS fabrication. The holes can be arranged in any layout form such as square, honeycomb, or any pattern.

Following is one of example for making the master mold. The integration of the microneedles 14 in the plates 12 and 13 includes (1) parallel alignment of the two plates 12 and 13, both having the same hole layout and (2) passing needles though the holes of the first plate and second plate, to the desired protrusion length beyond the second plate 12.

The protrusion length beyond the defining plate 12 is determined by the spacer 15 between the defining plate 12 and the needle tip alignment plate 16 positioned parallel to the defining plate at the protrusion length from the defining plate. The protrusion length will differ, depending in part on the desired length of the microneedle, and can range anywhere from 0.1 to 5000 µm, such as 0.5 to 250 µm, or 250 to 1500 µm, or any length between these ranges. The microneedle length above the defining plate 12 can be adjusted by changing the thickness of spacer 15 and again will depend on the desired length of the microneedle to be produced, and can range anywhere from 1 to 5000 µm, such as 1 to 250 µm, 250 to 1500 µm, or any length between these ranges. Unlike the positive unit master microneedles fabricated using MEMS or other CNC precision machining technology, the microneedle length is simply adjustable by adjusting spacer thickness and different lengths of microneedles in the same SSP can be designed by adjusting individual needles. This design of combining different lengths of microneedles can advantageously reduce the friction when penetrating into skin. Supporting plate 13 can be any structure to support the needles, such as a sponge material. The needles can be fixed to the plate 13 and/or the plate 12 with glue or other fixatives or adhesives.

The distance between needles will vary, depending on the size of the plate and the number of needles present. Typically, needles will be placed at a distance from 5 μm to 5000 μm from each other, such as from 100 to 3000 μm apart, 250 to 1000 μm apart, or any distance within these ranges. The plate can include any number of microneedles, such as 1 to 1,000,000, typically, 10 to 100,000, such as 50 to 10,000, 100 to 1000, or any number within these ranges.

Figure 1D:
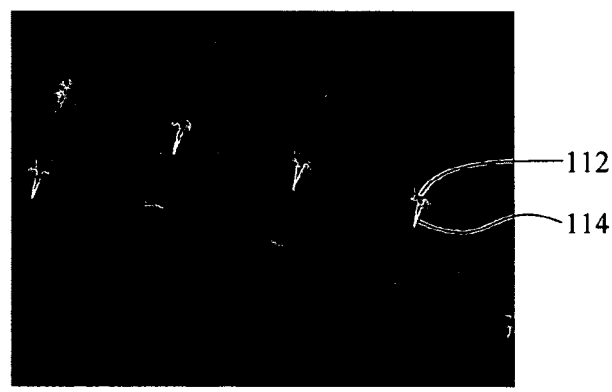
FIG. 1D is an actual image of the positive master from integrating and lining individual needles.

In an alternative embodiment, the holes in the defining plate, 12 are tapered with the same slope as the needle tip (FIG. 1B). The individual adjustment can be in the form of an addressable actuator array 18, where each actuator moves each individual needle (FIG. 1C). Actuator mechanisms and materials can be piezoelectric, electroactive polymers, thermal expansion, and electrochemical actuation. The actual image of a positive master with holes in the defining plate 112 and the needle tips 114 is shown in FIG. 1D.

A negative mold is made by casting from the positive master mold. Curable gel or castable polymer materials, such as uncured silicone or polydimethylsilozane (PDMS), are poured onto the positive master mold to produce a negative mold having the same surface contour as that of the positive master mold. Another method for preparing a negative mold is to dip the positive needle array into curable gel or thermoplastic materials directly without components 12, 15 and 16. In this case, the microneedle-shaped cavity of the negative mold is determined by the depth of the microneedle penetration in the curable gel, which is controlled using a spacer or a fine linear motion actuator.

Figure 1E:
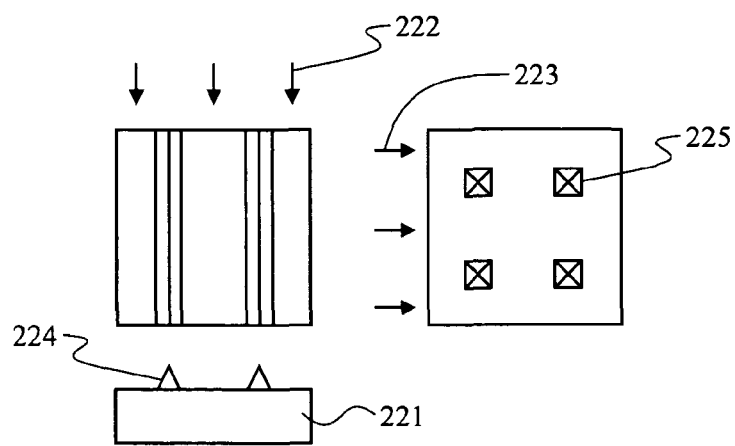
FIG. 1E shows a method for making pyramid microneedles by precision grinding.
Figure 1F:
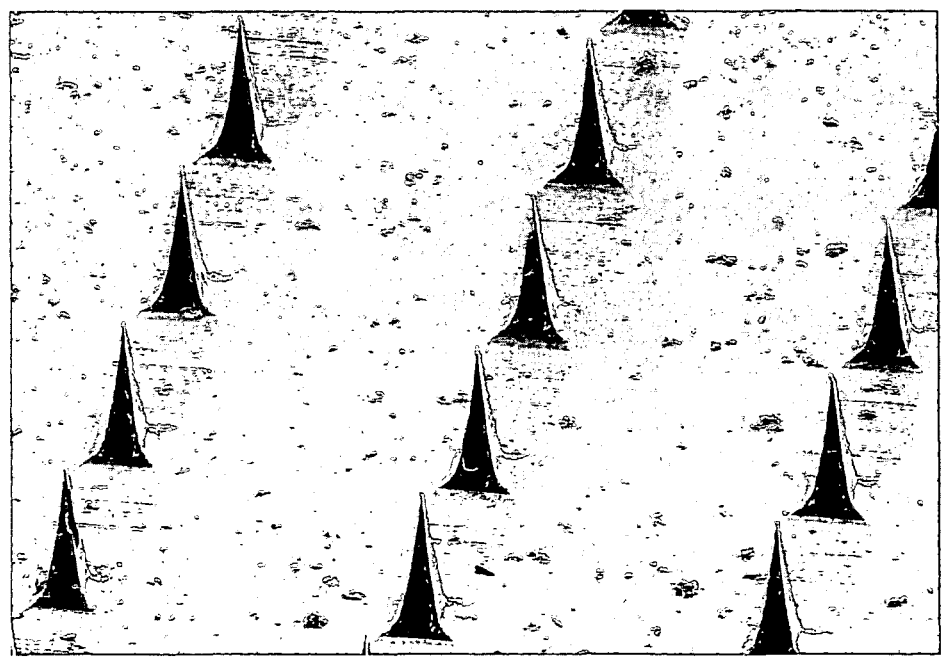
FIG. 1F shows a pyramid microneedle array cast from a negative mold made by precision grinding.

Another method for fabricating the positive micromold is precision tooling, such as by a computer numerical controlled (CNC) profile forming grinder. For example, a positive mold can be made by cutting across a block in at least two different directions to provide a mold comprising a base surface with a plurality of microneedles protruding form the base. See, e.g., U.S. Pat. No. 7,497,980, incorporated herein by reference in its entirety. Referring to FIG. 1E, the metal or formable base plate 221 can be repeatedly ground in a predetermined direction, such as 222, or 223 at a predetermined angle 224 to define the aspect ratio and the block plate can be removed to form an array of multi-faceted microneedles 225. FIG. 1F shows a dissolving pyramid microneedle array cast from a silicone secondary mold made from the positive master mold machined by a CNC profile forming grinder.

Figure 1G:
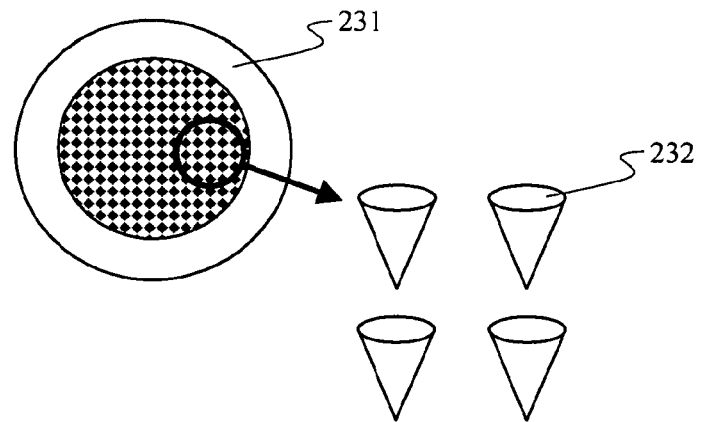
FIG. 1G shows a negative mold made by precision drilling.
Figure 1H:
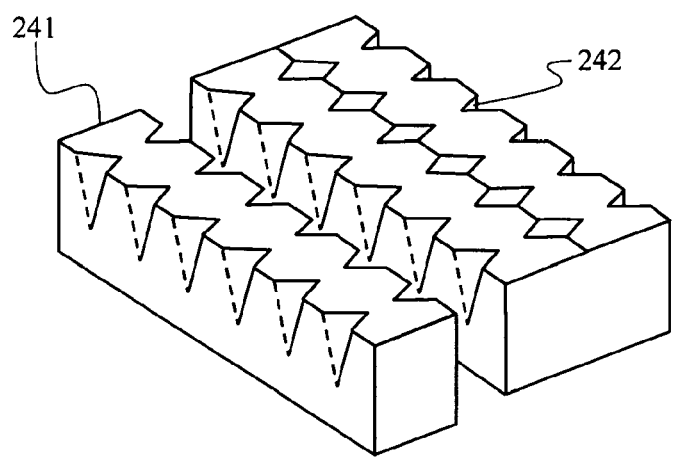
FIG. 1H shows a negative mold fabrication by precision grinding and laminating.

Another method to fabricate the positive master microneedle mold is to cast a microneedle array from a negative mold. The positive master microneedle cast can be any material if the material is castable and has a structural integrity suitable for following the cast. The microneedle array cast can be water nonsoluble, such as ethylcellulose or water-soluble, such as sodium carboxymethyl cellulose (SCMC). The negative mold can be made by CNC precision drilling, milling, or grinding. For example, a microcavity array 232 is drilled in Teflon plate 231 in FIG. 1G and used to produce an ethylcellulose positive master microneedle array. Referring to FIG. 1H, with a similar precision machining tool like a CNC profile forming grinder, the edge of plate 242 is cut at a predetermined shape and cut space, edges of the cut plates 241 are aligned and laminated to form the negative mold. Another method to make a negative mold is by casting any curable material such as PDMS from the positive master mold as described above.

Figure 2A:
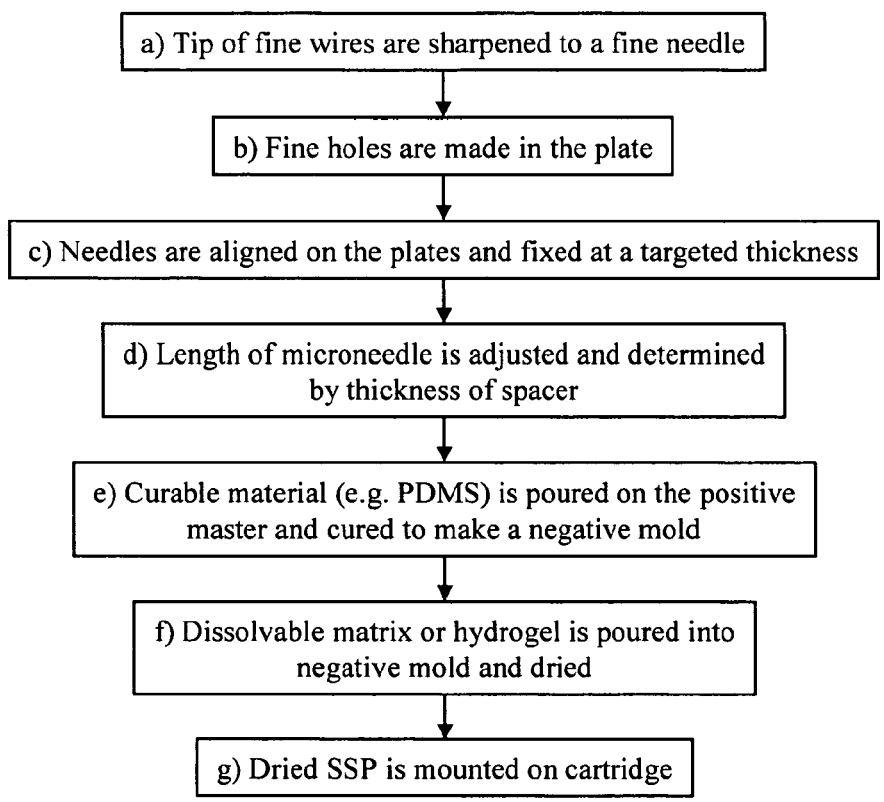
FIGS. 2A and 2B are flow charts of exemplary fabrication procedures for a solid perforator from positive and negative molds.
Figure 2B:
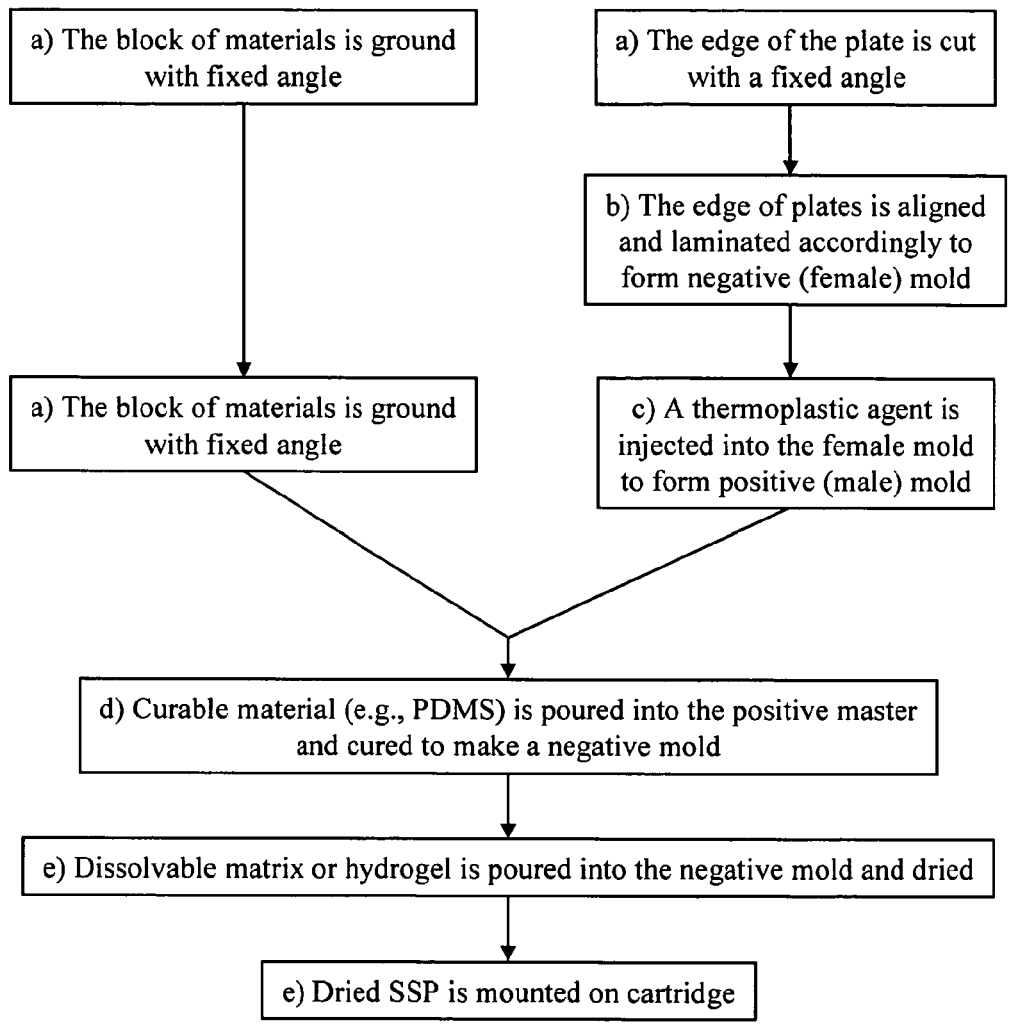

Flow charts for representative methods for preparing SSPs using the techniques described herein are shown in FIGS. 2A and 2B. Replication materials include polycarbonate, polymethyl methacrylate (PMMA), polyvinyl chloride, polyethylene (PE), and polydimethylsilozane (PDMS), and any thermally or chemically or light-activated cross-linking materials or thermoplastic materials. PDMS is the preferred mold material. PDMS precursors are generally a mixture of dimethylsilixane and a curing agent. One preferred material is medical grade silicone. The commercially available SYLGARD 184 (Dow Corning, Midland, Mich.), although not approved as a medical grade silicone to date, can be fully cured at 65° C.

A plastic mold including PDMS from this positive master is beneficial for making dissolvable SSPs because it is inexpensive, can be mass produced and provides an easy medium for removing microbubbles that might form in the hydrogel. A centrifuge process can be used for filling the hydrogel solution into the PDMS mold. The hydrogel easily fills into the tip of the mold without external pressure, especially when the silicone mold is in a vacuum. Without being bound by any particular theory, this may be due to the unique surface properties of PDMS and its compatibility with the hydrogel. Another possible explanation is that a vacuum is generated inside PDMS at low pressure and the internal vacuum particularly in the microneedle cavity wall region is a pulling force for filling the solution or gel into the tip of microneedle cavity. For mass production, a centrifuge or vacuum applied to the bottom of the negative mold, or a compressive force that pushes the gel into the microneedle cavity, may be used. As explained above, if a microbubble is trapped during mass production, ventilation provided at the bottom of the microneedle hole in the mold is beneficial. Optionally, the microhole or porous plates inside the microneedle cavity can be produced to ventilate the mold and prevent microbubble formation when the negative mold is used for making SSPs. Once the hydrogel is dried, the SSP is separated from the mold and cut for a component of a patch.

Fabrication of SSP

Figure 2C:
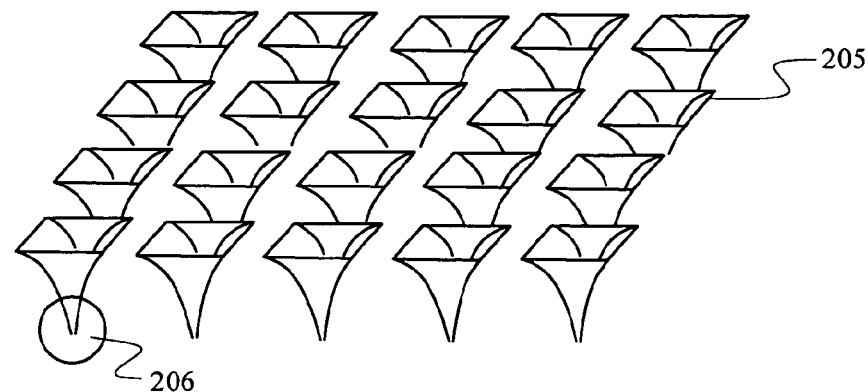
FIG. 2C is a schematic diagram of cavity with an open end.
Figure 2D:
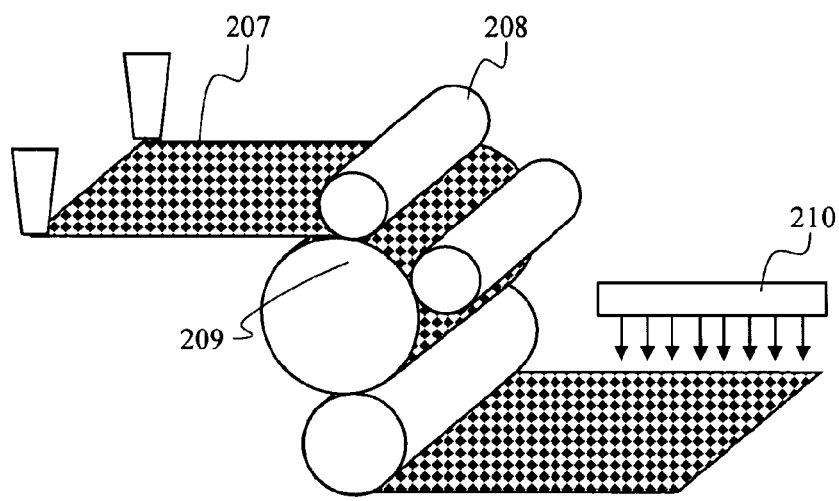
FIG. 2D is a schematic diagram of the cavity-fill process by using an open end cavity array.

A liquid solution, including the matrix material and including the selected drug(s) or drug-loaded particles, is cast in the negative mold, such as PDMS described above, and dried. Depending on the viscosity and other physical and chemical properties of the liquid solution, additional force such as centrifugal force, vacuum force, or a compression force may be used to fill the mold with optionally high temperature. To form a solid solution, the solvent can be air-dried, vacuum-dried, freeze-dried, convection oven dried or any other suitable drying method can be used. For continuous mass production, flexible plastic including PDMS silicone can be effectively utilized. Referring to FIG. 2C, the cavity tip of the negative mold is open 206 and lined up for continuous production. Since the tip is open, a vacuum from the bottom or external pressure from the top can easily fill the cavity with liquid solution. As shown in FIG. 2D, the gel is poured 207, cast, pressed 208, or optionally vacuumed 209 then dried 210. Once fully dried, an inexpensive plastic mold or silicone mold can be used as a packaging material. Both the microneedle and mold can be cut and combined until use.

Figure 2E:
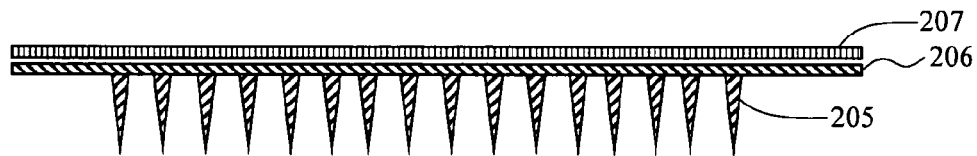
FIG. 2E is a schematic diagram of a sticky and flexible microneedle array.

It appears that the mold dimension does not determine the final dimension of the SSP because the solvent and water content is evaporated during the drying process. Therefore the final dimension of the SSP is smaller than the mold dimension. Optionally, multiple different layers in the microneedle can be fabricated with repeating casting/wiping of the same or different concentration of solid solution. When an adhesive layer is cast after the microneedle is formed, a sticky microneedle patch can be easily generated. For example, referring to FIG. 2E, a material, such as SCMC is cast and dried 205, then an adhesive layer is cast 206 and a soft baking layer made of silicone or another soft hydrogel is cast 207. Using a multiple casting technique, a sticky and flexible microneedle patch is produced. The dried SSP is separated from the mold and cut to an appropriate shape and size for a patch component. For a description of representative shapes and sizes of such perforators, see, e.g., U.S. Pat. Nos. 6,945,952, 7,182,747 and 7,211,062, incorporated herein by reference in their entireties.

Suitable matrix materials for an SSP perforator include dissolvable polymers, including but not limited to sodium carboxymethyl cellulose (SCMC), sodium hyaluronate (HA), polyvinylpyrolidone (PVP), polyethylene glycol (PEG), polyvinyl alcohol (PVA), polyethylene oxide (PEO), polyacrylic acid, polystyrene sulfonate, polypeptide, cellulose, hydroxypropyl cellulose (HPC), hydroxyethyl cellulose (HEC), hydroxypropyl methylcellulose (HPMC), dextrin, dextran, mono- and polysaccharide, polyalcohol, gelatin, gum arabic, alginate, chitosan cylcodextrin, carbohydrate and other water dissolvable natural and synthetic polymer and combinations of the above.

Carbohydrate derivatives, such as sugar derivatives (for example, trehalose, glucose, maltose, lactose, sucrose, maltulose, iso-maltulose, lactulose, fructose, turanose, melitose, mannose, melezitose, dextran, maltodextrin, icodextrin, cyclodextrin, maltotol, sorbitol, xylitol, inositol, palatinit, mannitol, stachyose and raffinose) can be used or mixed with above. Depending on the physical and chemical properties of each component, the mechanical properties and dissolution rate can be designed by using a combination of above. The carbohydrate can be melted to form microneedles from the mold or dissolved with a water soluble polymer as described above. Once dried and separated from the mold, an additional drying process (post drying-treatment) can be used or water content removed. In this way, the mechanical strength of the microneedles is increased or adjusted and compression strength of microneedles can be controlled.

Water-soluble ingredients, such as phosphate, nitrate and carboxylate glasses, magnesium chloride, potassium chloride and calcium chloride can also be used for a matrix material, alone or mixed with a matrix polymer. This component can be used for stabilizing or enhancing the drug delivery or vaccination capability. For vaccination, undissolvable particles, such as depot adjuvants, can be mixed in the matrix. The matrix can also include vitamin C or vitamin C derivatives. Vitamin C can diminish potential skin reactions. It has been observed that adding vitamin C reduces viscosity of the matrix to achieve a better filling of the mold.

Optionally, the surface properties of the mold can be modified by various techniques, such as silanization, corona treatment, plasma treatment, surface coating, polymer surface grafting etc., in order to improve the compatibility of the gel with the mold and to provide for easy separation of the gel when dried. It has been observed by the present inventor that PDMS molding is very compatible with SCMC hydrogels and microbubbles do not form.

Fabrication of SSP Patch Cartridge and Applicator

Figure 3A:
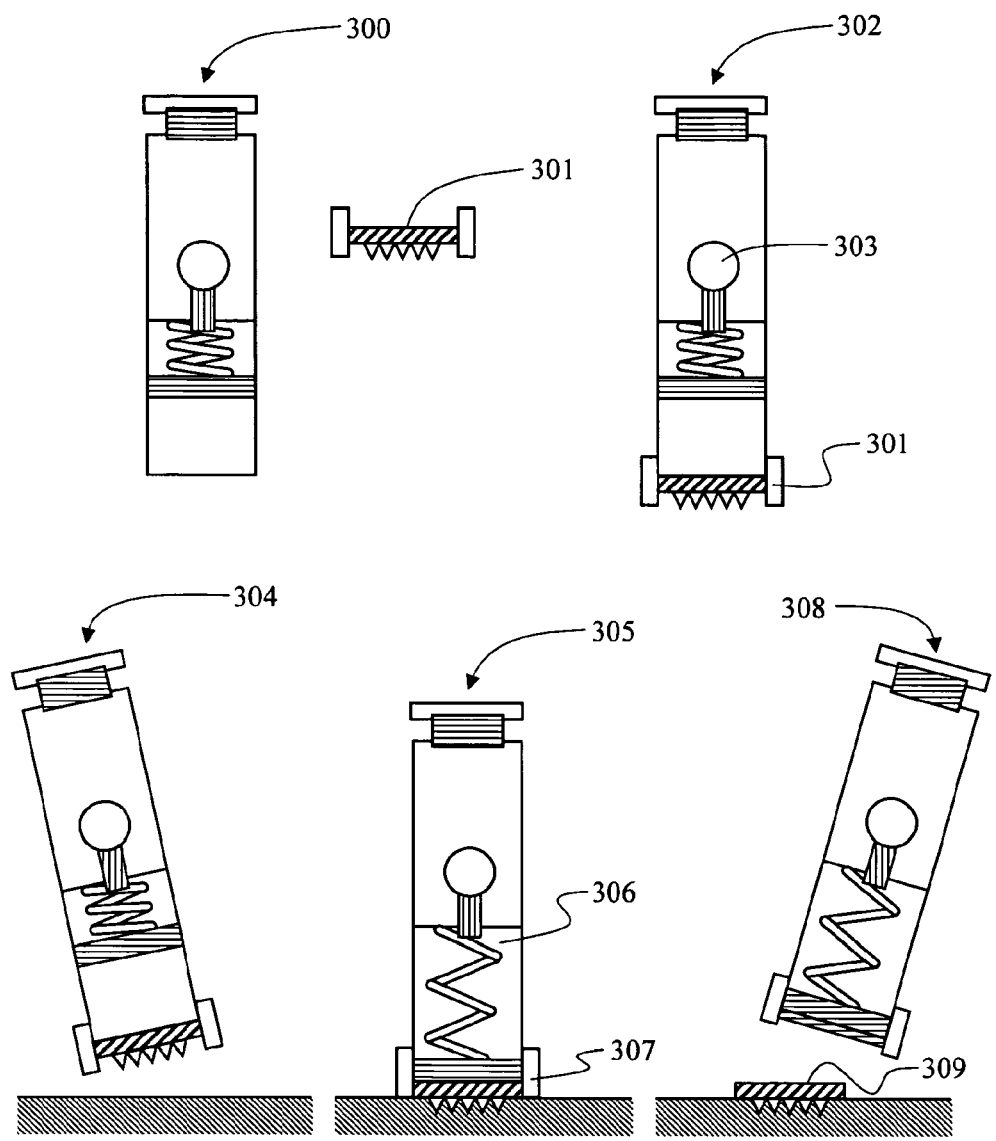
FIG. 3A is a schematic diagram of the use of an injector according to the present methods.

The patch made using the methods described herein is applied to the skin preferably using an injecting device (applicator). FIG. 3A demonstrates patch application with a spring-driven applicator. The cartridge 301 with the solid solution patch can be loaded on an applicator with a compressed spring 300, to result in a loaded spring compressed applicator 302 that includes a spring trigger 303. In this embodiment, the user can administer the microneedle patch alone without aid. The occlusive flat form of the cartridge has the advantages of volume reduction in storage and transport. In the flat form cartridge, the piston of the applicator strikes the patch laying on the skin, which may maximize the striking force or impact energy to help the SSP penetrate consistently into target skin. The cartridge can protect the SSP both physically and chemically from the environment until used. An easily ruptureable or tearable film or membrane can protect the SSP in the cartridge. In an embodiment where a flat cartridge is used, microneedles are contacted or placed in close proximity to the skin and then the piston part of the applicator impacts the microneedle array against the skin. This microneedle insertion mechanism is equivalent or better than when the microneedles are placed on the skin with a large gap between the microneedle and the targeted skin.

Figure 3B:
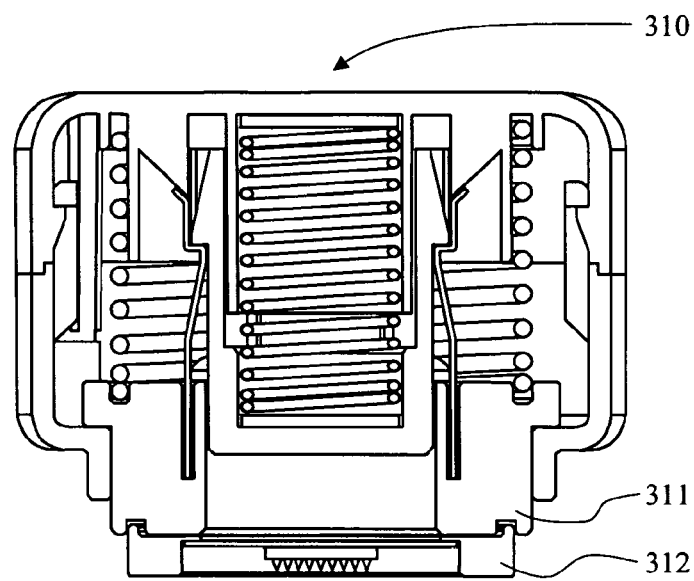
FIGS. 3B and 3C are diagrams of a push-button (FIG. 3B) and mouse style (FIG. 3C) injector, respectively.
Figure 3C:
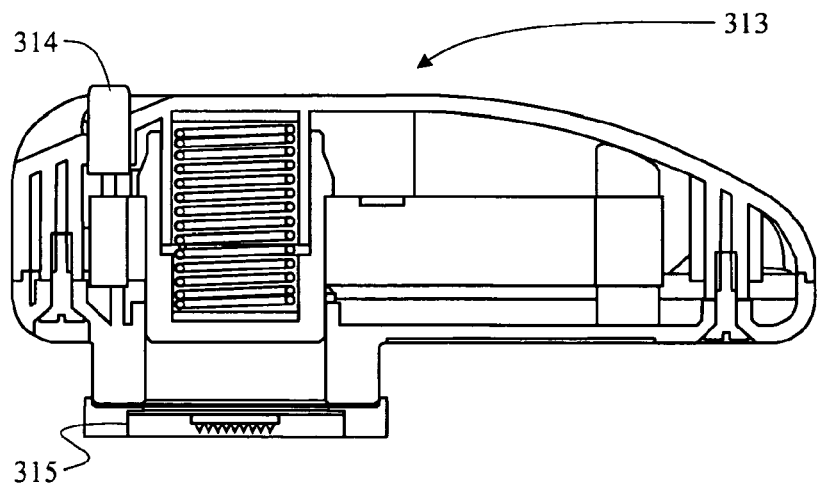
Figure 3D:
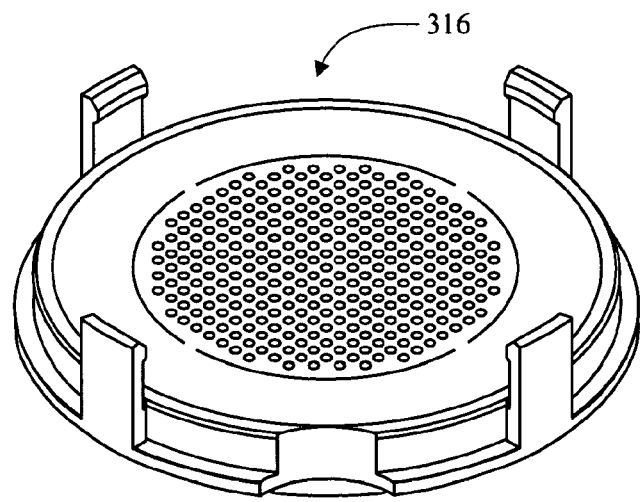
FIGS. 3D and 3E are top view (FIG. 3D) and cross-sectional view (FIG. 3E), respectively, of a cartridge attachable to an injector.
Figure 3E:
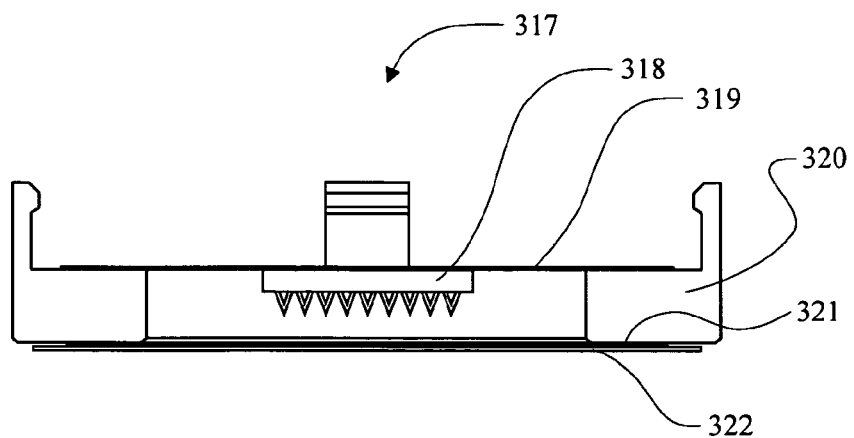
Figure 3F:
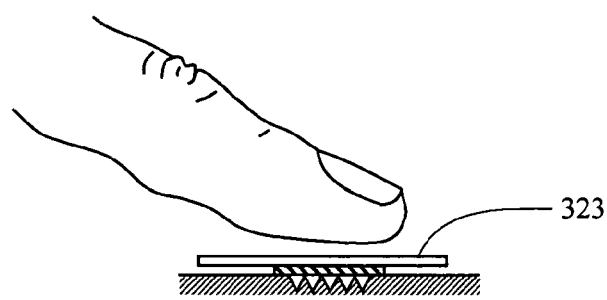
FIG. 3F is a side view of insertion with a pressure sensing film.

FIGS. 3B and 3C show additional examples of applicators, push-button style 310 (FIG. 3B) and mouse style 313 (FIG. 3C), respectively. The microneedle cartridge 312 can be attached to applicator 310 and the trigger 311 is activated when pushed. In the mouse style applicator 313, the trigger 314 is on top of the mouse. A top and side view of a cartridge is depicted in FIGS. 3D and 3E, respectively. The microneedle 318 is held on a rupturable membrane 319 inside a disposable plastic case 320 and is protected by occlusive film 322 on the 321 surface. FIG. 3F shows a mode of insertion using a pressure sensing film 323.

Drug Delivery by SSP

Figure 4:
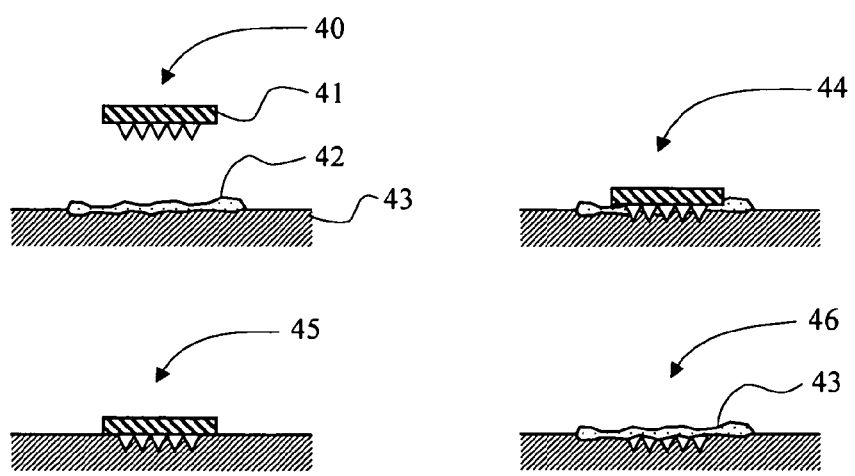
FIG. 4 is an example of skin treatment before and/or after patch administration.

FIG. 4 shows another example of patch application with formulated gel that includes a cream and/or lotion. This formulated gel can contain one or more active ingredients which are the same or different from the active ingredients in the SSP, depending on the application. The formulated gel can contain beneficial agents for skin such as a humidifying excipient or anti-irritant or anti-bacterial agents. In this example 40, the formulated gel 42 is applied on the target skin 43 prior to patch application. The patch application on pretreated the skin is depicted in 44. In 45 and 46, the patch is applied to the skin and after SSPs are dissolved, the formulated gel is applied on the sites 43. In this case, the active ingredient in the gel can be delivered through the pores created by patch insertion and dissolution.

SSP

The SSP perforators can have straight or tapered shafts or can be corn-shaped, pyramids, wedges or blades, as predetermined by the positive master. In a preferred embodiment, the outer diameter of an SSP perforator is greatest at the base or second end, about 1-2000 µm, and the perforator outer diameter near the first end is preferably 1-100 µm. The length of an SSP perforator is typically in a range 10-5000 µm, more preferably in a range 100-2000 µm. Skin is not a smooth surface, but rather has a rugged surface and has different depths microscopically. In addition, the thickness of the stratum corneum and elasticity of the skin varies from person to person and from location to location on any given person's body. A desirable penetration depth has a range, rather than a single value, for effective drug delivery and relatively painless and bloodless penetration. Penetration depth of an SSP perforator can affect pain as well as delivery efficiency. In certain embodiments, the perforator penetrates to a depth in the range of 10-1000 µm. In transdermal applications, the "penetrated depth" of the SSP perforator is preferably less than 500 µm so that a perforator, inserted into the skin through the stratum corneum, does not penetrate past the epidermis. This is an optimal approach to avoid contacting nerves and blood vessels. In such applications, the actual length of the SSP perforator can be longer because the basal layer associated with the SSP system may not be fully inserted into the skin because of elasticity and the rough surface of the skin.

Depending upon medical needs, perforator penetration to the dermis layer may be required in some applications. In these instances, use of an SSP system can be a practical option in handling instant drug delivery situations. The penetrating portion of an SSP perforator can be optimized by adjusting perforator variables (SSP length, dimension, mechanical properties of the basal or substrate layer as well as stroke and speed of insertion of an SSP perforator), as well as accounting for target skin elasticity, skin hardness and surface roughness. The primary functions of an SSP perforator are to pierce the stratum corneum, to provide instant initiation of drug delivery from the matrix and optionally to help keep the channels open for subsequent gel or cream or lotion application or from a reservoir. As long as an SSP perforator dissolves reasonably quickly and is strong enough to pierce the stratum corneum, any biocompatible material can serve as an SSP perforator. In some applications, a non-dissolving microneedle is useful. In this case, a water-insoluble hydrogel such as ethylcellulose, can be used in the above-described fabrication method.

Figure 5A:
FIGS. 5A and 5B are actual images of an SSP.
Figure 5B:
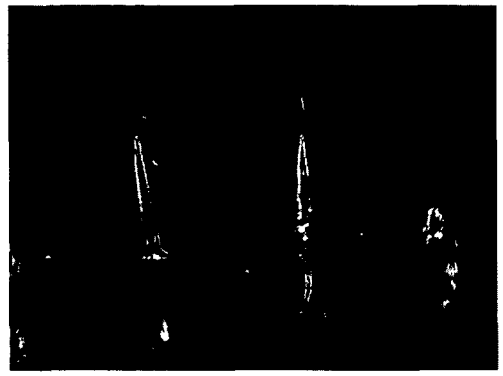

In some cases, concentrating drug at the tip portion of the SSP is desirable. Such an SSP can be designed by a multiple casting/wiping method and/or particle concentrating methods as described previously. FIGS. 5A and 5B show an actual image of an SSP composed of sodium methyl cellulose using a silicone negative mold. In another embodiment, the flexible and sticky base with the microneedle array can be simply fabricated as described above. For example, SCMC fills the microneedle mold and an adhesive layer is cast and a soft hydrogel formulation are cast sequentially. The resulting patch is a hard microneedle and a sticky/soft basal microneedle array which does not require other adhesive backing film or overlay.

SSP Patch Systems

An SSP patch system optionally includes a reservoir containing a liquid or gel form of the second drug and one or more perforators extending from at least a part of the reservoir's surface. The SSP perforators associated with the patch system penetrate the stratum corneum of the skin to enhance percutaneous drug administration and to provide prompt drug delivery. When drug is dispersed in the basal layer, sustained delivery of the drug from the basal layer can be achieved using a backing film. In the patch system, the SSP perforators and the reservoir can be constructed as a single unit or as separate units.

An SSP patch system is applied to the skin so that one or more SSP perforators penetrate through the stratum corneum, into the epidermis or into the dermis depending on the application. In an alternative approach, an SSP and gel, cream and/or lotion are used. For example, the gel can include a drug and/or desired excipients and can be applied or spread at the desired sites. An SSP patch is subsequently inserted. Alternatively, the gel can be applied after patch use.

An SSP system can transport therapeutic and/or prophylactic agents, including drugs and vaccines and other bioactive molecules, across or into skin and other tissues. An SSP device permits drug delivery and access to body fluids across skin or other tissue barriers, with minimal damage, pain and/or irritation at the tissue. In drug delivery applications, an SSP perforator is primarily composed of an active drug (or drug particle itself) and a composition of gel (including cream and lotion) can be designed depending on a desired drug profile. Depending on the application, an osmotically active or anti-irritant compound or anti-bacterial agent, can have a beneficial effect. In diagnostic applications, the SSP perforator can include or consist of sensor materials loaded that react to the presence of specific analytes or metabolites. In order to vary or control the drug delivery rate, an external physical enhancement system, using iontophoresis, electrophoresis, sonophoresis, piezoelectric response, a heating element, magnetic element, or a similar response or combination of above, can be provided with the overlay layer.

Drugs to be Delivered by SSP System

Delivered drugs can be proteins, peptides, nucleotides, DNA, RNA, siRNA, genes, polysaccharides, and synthetic organic and inorganic compounds. Representative agents include, but are not limited to, anti-infectives, hormones, growth regulators, drugs regulating cardiac action or blood flow, and drugs for pain control. The drug can be for vaccination or local treatment or for regional or systemic therapy.

Many drugs can be delivered at a variety of therapeutic rates, controlled by varying a number of design factors including: dimensions of the SSP, drug loading in the SSP, dissolving rate of the matrix, number of SSP perforators, size of the SSP patch, size and composition of the gel (including creams and lotion), and frequency of use of the device, etc. Most applications of SSP drug transdermal delivery target the epidermis, although delivery into blood stream directly is available by extending the penetration length of an SSP patch.

The SSP patch systems disclosed herein are also useful for controlling transport across tissues other than skin. Other non-skin tissues for delivery include nasal or vaginal, buccal, ocular, dental regions or inside a tissue with the aid of a laparoscope or into other accessible mucosal layers to facilitate transport into or across those tissues. For example, an SSP patch can be inserted into a patient's eye to control or correct conjunctiva, sclera, and/or cornea problems, to facilitate delivery of drugs into the eye with a slow moving actuator. The formulated drug stays in the tissue for sustained drug delivery even after the patch is removed. An SSP patch can also be inserted into the oral cavity including buccal membrane for rapid systemic drug delivery or short delivery duration for example breakthrough pain management and for dental treatment applications. A drug may be delivered across the buccal mucosa for local treatment in the mouth or gingiva to act as a muscle relaxant for orthodontic applications. As another example, SSP systems may be used internally within the body on, for example, the lining of the gastrointestinal tract to facilitate uptake of orally-ingested drugs or at the lining of blood vessels to facilitate penetration of drugs into the vessel wall. In the case of internal tissue application, use of a bioadhesive SSP material can help the SSP stay in place longer. A food patch including essential amino acids, fats and vitamins can be used, such as in emergencies.

Intradermal Drug Delivery Applications

Another important application is vaccination and for treating and preventing allergies. The skin is an ideal site for effective vaccine delivery because it contains a network of antigen presenting cells, such as Langerhans and dermal dendrite cells. An SSP system for skin immunization can reduce vaccine dose and induce rapid delivery to skin dendrite cell and can provide a depot effect for better vaccination. The SSP system can be easily designed for multivalent vaccines and is expected to provide more stability than the liquid form vaccine in transportation and storage.

Another important use of the subject invention is for cosmeceutical applications. An SSP system with particles can be used efficiently and safely to remove or reduce wrinkle formation, skin aging hyperhidrosis and hair loss. For example, Botulisum toxin (Botox), hydroxyacid, vitamins and vitamin derivatives, Epidermal Growth Factor (EGF), Adenosine, Arbutin, and the like, can be delivered using the systems described herein. The systems are also useful for treating lesions or abnormal skin features, such as pimples, acne, corns, warts, calluses, bunions, actinic keratoses and hard hyperkeratotic skin, which is often found on the face, arms, legs or feet. An SSP system is also useful as a tattoo-creating/removing patch for cosmetic application. Active or sham SSP systems can also be used for acupuncture.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Fabrication Positive Master and SSPS from Silicone Mold

Holes were made in glass as shown in FIG. 1D by chemical etching through holes on a photoresist film patterned by photolithography and acupuncture needles were aligned through the holes 114. The tip of the needles through the holes are depicted. PDMS was poured on this side and cured overnight. 8% sodium methyl cellulose hydrogel was poured on this silicone mold and centrifuged at 3,000 rpm for 5 minutes. After centrifuging, the hydrogel was dried for one day and separated from the mold. FIG. 5 is the image of dissolvable microneedle made of cellulose. Another micromold from CNC profile forming grinding techniques is depicted in FIG. 1F.

Example 2

Compression Break Force and Dissolution Time with Various Compositions

Compression testing was done with a force gauge (Nexy-Gen DF series) and the conical compression force applied until the microneedles broke was measured. The test samples were prepared with various sugar derivatives and sodium carboxy methyl cellulose (SCMC). The 8% SCMC was mixed with DI water. The dissolution time for to fully dissolve the SCMC in 10 ml of DI water at 300 rpm was measured. Since the sugar derivatives were added to the fixed 8% SCMC hydrogel, the results were normalized over weight. Results are shown in Table 1.

TABLE 1

| Formulation composition (SCMC:Lactose) | Dissolution time (min) | Conical compression force (N) |
|---|---|---|
| SCMC = 100 | 10.81 ± 0.03 | 11.27 ± 0.75 |
| SCMC:Trehalose = 91:9 | 10.73 ± 0.63 | 17.13 ± 1.95 |
| SCMC:MaltoDextrin = 91:9 | 10.25 ± 0.39 | 15.23 ± 5.24 |
| SCMC:Sucrose = 91:9 | 11.00 ± 1.01 | 17.77 ± 1.08 |
| SCMC:PVP = 91:9 | 11.21 ± 0.94 | 19.50 ± 6.66 |
| SCMC:Glucose = 91:9 | 10.59 ± 1.88 | 10.61 ± 0.23 |
| SCMC:Mannitol = 91:9 | 11.07 ± 0.86 | 16.15 ± 0.52 |
| SCMC:Sorbitol = 91:9 | 11.09 ± 1.95 | 15.43 ± 0.62 |
| SCMC:Lactose = 91:9 | 10.55 ± 0.24 | 18.03 ± 2.50 |

Example 3

Mechanical Properties with Different Lactose Compositions

Compression and dissolution tests were done on various compositions of lactose. As lactose was added, the test article dissolved faster and compression force increased. See, Table 2.

TABLE 2

| Formulation composition (SCMC:Lactose) | Dissolution time (min) | Conical compression force (N) |
|---|---|---|
| SCMC:Lactose = 100:0 | 10.81 ± 0.03 | 11.27 ± 0.75 |
| SCMC:Lactose = 91:9 | 10.55 ± 0.24 | 18.03 ± 2.50 |
| SCMC:Lactose = 83:17 | 8.68 ± 0.13 | 23.25 ± 0.21 |
| SCMC:Lactose = 77:23 | 7.87 ± 0.45 | 21.87 ± 3.62 |
| SCMC:Lactose = 71:29 | 7.03 ± 0.14 | 29.93 ± 6.94 |
| SCMC:Lactose = 67:33 | 7.02 ± 0.61 | 23.90 ± 13.75 |
| SCMC:Lactose = 62:38 | 7.79 ± 0.05 | 39.57 ± 2.19 |
| SCMC:Lactose = 44:56 | 6.57 ± 0.03 | 24.47 ± 1.11 |
| SCMC:Lactose = 29:71 | 4.58 ± 0.75 | 45.56 ± 4.29 |
| SCMC:Lactose = 21:79 | 3.91 ± 0.65 | 75.25 ± 2.20 |

Example 4

Combination Treatment of SSP and Gel in Acne Treatment

Figure 6:
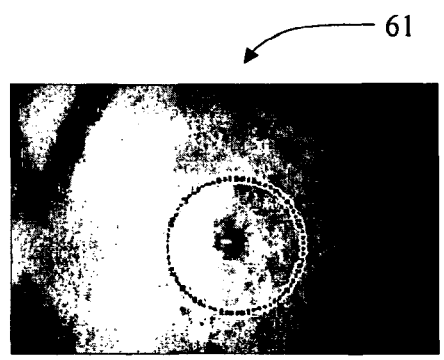
FIG. 6 is the actual image of acne treatment with gel and SSP patch treatment.
Figure 6:
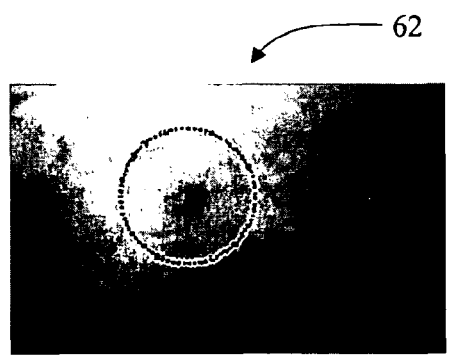

To treat acne, a benzoyl peroxide microneedle patch was applied followed by the application of an acne gel. The acne severity decreased significantly and rapidly after microneedle patch and gel treatment. As shown in FIG. 6, the combination treatment appeared more effective than the microneedle patch. The treated acne sites became soft and smooth after all treatments. The combination treatment is practical. For example, the SSP can be applied at night with subsequent gel application during the day.

Example 5

Microparticle-Concentrated Microneedle Tip

Two casting steps were carried out as follows. First, the gel-containing microparticles were spun on the mold, immediately followed by removal of the gel from the exterior of the cavities while leaving the gel in the cavities. In the second coating, the gel made of excipients without the microparticle was added on the vaccine layer. The amount of microparticle was determined by their concentrations in the first layer gel and the volume of the total cavities in the patch.

Example 6

Vacuum Treatment of Silicone Mold for Filling Cavity with Gel

Silicone molds were put in the vacuum of 27 inch Hg to generate vacuum inside the silicone. Then, SCMC gel with 10% lactose was coated on the mold. Air in the cone-shaped cavities under the gel layer was slowly removed into the silicone body, pulling down the SCMC gel on the mold into the cavities, and finally filling down to the cavity tip. DI water was used in the same test. Experimental parameters and results are given below.

1. Materials:
silicone mold 3 mm thick, cone-shape cavities of 1.5 mm depth and 0.67 mm entry diameter 2. SCMC Gel

| Vacuum time (min) | Cavity fill-up time (min.) |
| --- | --- |
| 1 | Not filled until 28 min. |
| 3 | 11 |
| 7 | 5 |

3. DI Water

| Vacuum time (min) | Cavity fill-up time (min.) |
| --- | --- |
| 1 | Not filled until 28 min. |
| 3 | 9 |
| 7 | 4 |

Thus, SSP systems using drug and drug-loaded gels and the fabrication and use thereof has been described. Although preferred embodiments of the subject invention have been described in some detail, it is understood that obvious variations can be made without departing from the spirit and the scope of the invention as defined by the claims herein.

The invention claimed is:

1. A method of manufacturing a microneedle array, the method comprising:
   (a) preparing a positive master mold comprising a plurality of microneedles penetrating through a defining plate to extend from a bottom surface thereof, wherein the plurality of microneedles are spaced from one another at a predetermined distance;
   (b) individually adjusting at least some of the plurality of microneedles by an actuator array individually moving the at least some microneedles through the defining plate to extend different distances from the bottom surface thereof, thereby providing a desired surface contour to the master mold;
   (c) preparing a negative mold having a negative surface contour that is the reverse of the desired surface contour of the positive master mold by shaping a curable gel or thermoplastic material against the bottom surface of the defining plate having the adjusted microneedles;
   (d) preparing a microneedle array having a surface contour that is the reverse of the negative surface contour of the negative mold by shaping a dissolvable polymer against the negative mold; and
   (e) drying the microneedle array.

2. The method of claim 1, wherein the curable gel or thermoplastic material is uncured silicone.

3. The method of claim 1, wherein the curable gel or thermoplastic material is polydimethylsilozane (PDMS).

4. The method of claim 1, wherein the dissolvable polymer is a hydrogel.

5. The method of claim 4, wherein the hydrogel comprises sodium carboxymethyl cellulose (SCMC).

6. The method of claim 1, wherein the dissolvable polymer holds a selected drug.

7. The method of claim 1, further comprising applying a vacuum, centrifugal, or compressive force to the negative mold to fill the negative mold with the dissolvable polymer and/or with a selected drug.

8. The method of claim 1, further comprising separating the dried microneedle array from the negative mold.

9. The method of claim 1, wherein the method further comprises casting an adhesive layer between microneedles of the microneedle array.

10. The method of claim 1, wherein the method further comprises incorporating vitamin C into the dissolvable polymer.

11. The method of claim 1, wherein the method further comprises creating a micro-hole at a location through the negative mold.

12. The method of claim 1, wherein said shaping of the curable gel or thermoplastic material is conducted either by casting or by dipping.

13. A method of manufacturing a microneedle array system, the method comprising:
   (a) manufacturing a microneedle array according to the method of claim 1; and
   (b) mounting the microneedle array in a cartridge for delivery to skin.

14. The method of claim 13, wherein the cartridge is in association with an injector.

* * * * *